United States Patent
Hadizadeh Hafshejani et al.

(10) Patent No.: US 10,333,541 B1
(45) Date of Patent: Jun. 25, 2019

(54) NON-UNIFORM SAMPELING

(71) Applicants: Ehsan Hadizadeh Hafshejani, Vancouver (CA); Ali Fotowat-Ahmady, Great Falls, VA (US); Kiomars Anvari, Walnut Creek, CA (US)

(72) Inventors: Ehsan Hadizadeh Hafshejani, Vancouver (CA); Ali Fotowat-Ahmady, Great Falls, VA (US); Kiomars Anvari, Walnut Creek, CA (US)

(73) Assignee: Kiomars Anvari, Walnut Creek, CA (US)

( * ) Notice: Subject to any disclaimer, the term of this patent is extended or adjusted under 35 U.S.C. 154(b) by 0 days.

(21) Appl. No.: 16/114,346

(22) Filed: Aug. 28, 2018

(51) Int. Cl.
*H03M 1/12* (2006.01)
*A61B 5/00* (2006.01)
*H03M 1/56* (2006.01)
*H03M 1/54* (2006.01)
*H03M 1/52* (2006.01)

(52) U.S. Cl.
CPC ......... *H03M 1/1265* (2013.01); *A61B 5/7203* (2013.01); *H03M 1/12* (2013.01); *H03M 1/124* (2013.01); *H03M 1/126* (2013.01); *H03M 1/1245* (2013.01); *H03M 1/52* (2013.01); *H03M 1/54* (2013.01); *H03M 1/56* (2013.01)

(58) Field of Classification Search
CPC .... H03M 1/1245; H03M 1/126; H03M 1/124; H03M 1/52; H03M 1/54; H03M 1/56; H03M 1/12
USPC .......................... 341/122, 123, 124, 127, 155
See application file for complete search history.

(56) References Cited

U.S. PATENT DOCUMENTS

2012/0293350 A1* 11/2012 Redfern .................. H03M 1/18
341/122

* cited by examiner

Primary Examiner — Joseph J Lauture

(57) ABSTRACT

A novel non-uniform sampling technique for a burst type signal. The analog signal is digitized with high sampling rate to maintain harmonics at higher frequencies and consequently the integrity of the analog signal. Then by using non-uniform sampling technique the most significant samples are selected for further processing which results in overall cost and power consumption reduction.

8 Claims, 14 Drawing Sheets

Figure 4  Sub-Harmonic IF Sampling

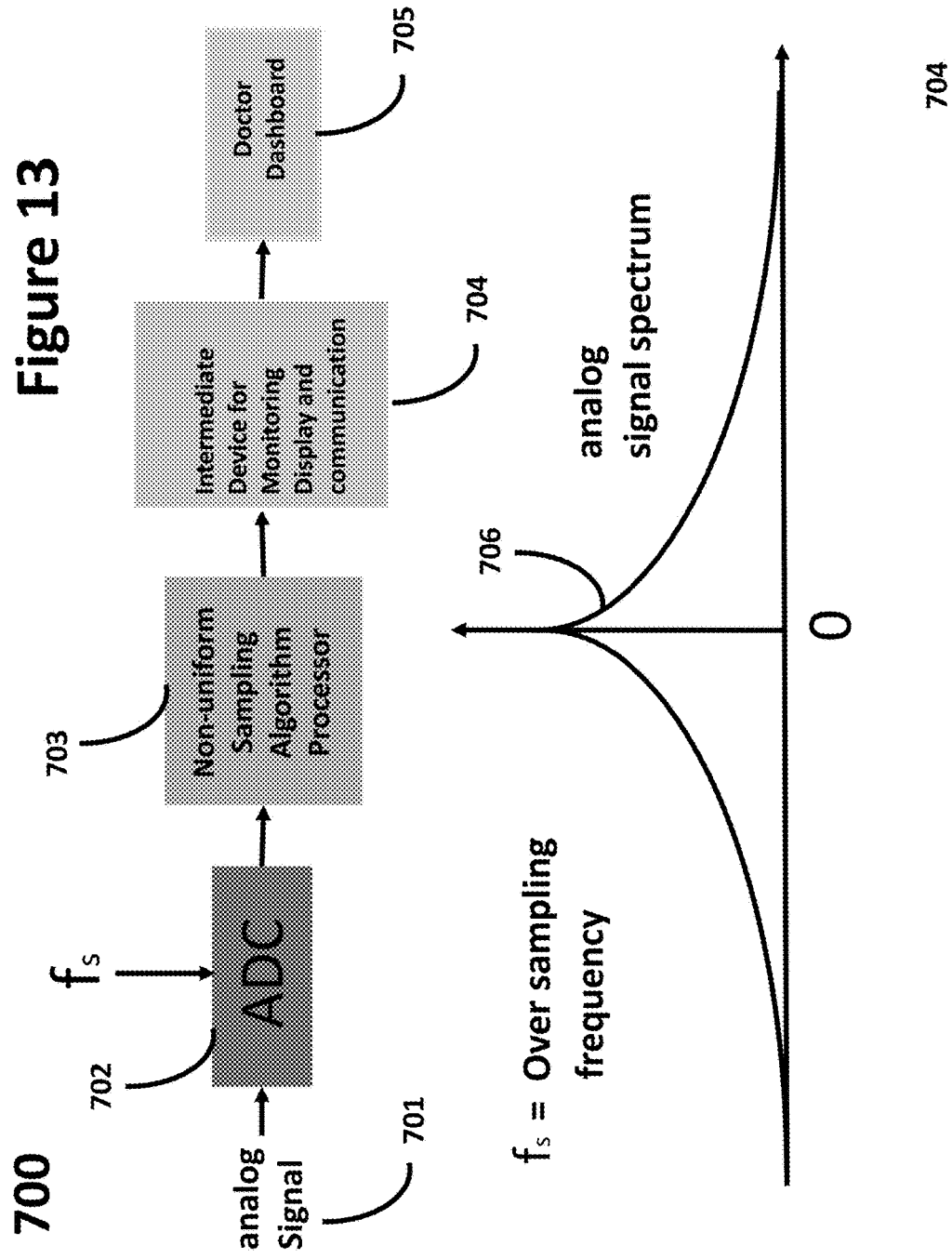

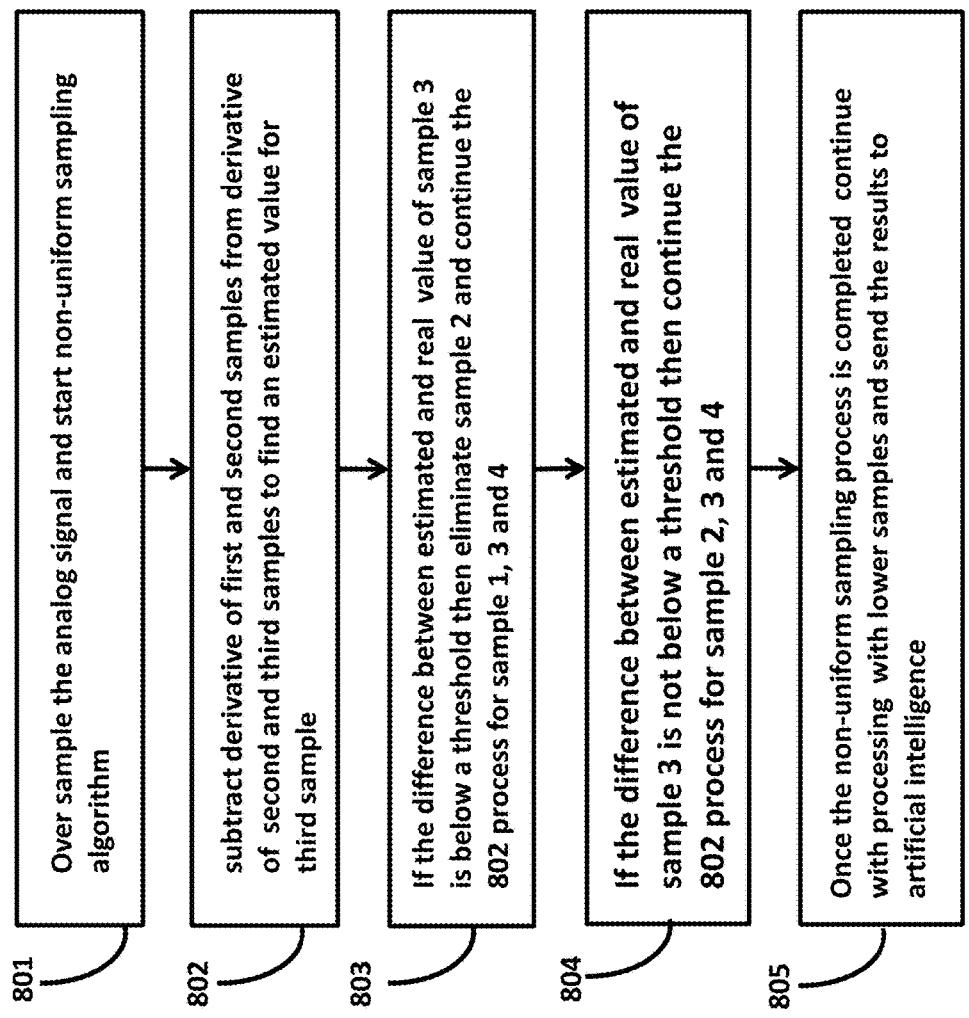

NON-UNIFORM SAMPELING

BACKGROUND

In the field of digital signal processing, the sampling theorem is a fundamental bridge between continuous-time signals (often called "analog signals") and discrete-time signals (often called "digital signals"). It establishes a sufficient condition for a sample rate that permits a discrete sequence of samples to capture all the information from a continuous-time signal of finite bandwidth.

The continuous analog data must be sampled at discrete intervals that must be carefully chosen to ensure an accurate representation of the original analog signal. It is clear that the more samples taken (faster sampling rate), the more accurate the digital representation, but if fewer samples are taken (lower sampling rates), a point is reached where critical information about the signal is actually lost.

The Nyquist Theorem, also known as the sampling theorem, is a principle that engineers follow in the digitization of analog signals. For analog-to-digital conversion to result in a faithful reproduction of the signal, according to the Nyquist Theorem, the sampling rate must be at least twice the highest analog frequency component as shown in FIG. 1.

There are times that the analog signal spectrum is slightly shifted from the zero Hz frequency as shown in FIG. 2. This type of signal is called low intermediate frequency (IF) signal. In this case there are two approaches. One is to shift the analog signal spectrum to zero Hz in analog domain and then similar to FIG. 1 use Nyquist sampling and digitize the analog signal. In the first approach there is need for analog circuitry for shifting the spectrum to zero Hz which results in cost and power consumption. In a second approach Nyquist theorem is used to digitized the low IF analog signal and then shift the spectrum in digital domain to zero Hz. This approach requires higher sampling rate, a higher rate analog-to-digital convertor and slightly signal processing in digital domain.

In another scenario the analog signal is centered at a high IF frequency as shown in FIG. 3. In this scenario there are three solutions. One similar to low IF down convert the analog signal to zero Hz frequency and then digitized. Again this approach results in cost and power consumption. The second approach is to sample the high IF analog signal which requires very high rate analog-to-digital convertor and considerable signal processing that results in cost and power consumption. The third approach is to use sub-harmonic sampling. In sub-harmonic sampling in order to be able to recover analog signal information in digital domain the sampling rate should be equal or higher than twice the bandwidth of the analog signal. The choice of the sampling rate needs to simplify the required signal processing in digital domain. FIG. 4 demonstrate how sub-harmonic sampling is used to digitize and subsequently shift the digital signal to zero Hz for a complex signal with real and imaginary components.

If the sampling rate is smaller than what was defined above, then a phenomenon called aliasing will occur in the analog signal bandwidth as shown in FIG. 5. It can be seen that aliasing affects the dynamic range of the signal since the upper part of the signal spectrum is affected. This condition will result in reduction in overall signal-to-noise at the higher frequencies, and could result in the distortion due to aliased out-of-band tones or harmonics as shown in FIG. 5.

It should be cleared by now, that for a given analog input bandwidth; the requirements for anti-aliasing filter are related not only to the sampling rate, fs, but also to the desired system dynamic range. For burst type analog signals that have harmonics spread over a very large bandwidth like the one shown in FIG. 6 defining the requirements of the anti-aliasing filter is even more difficult. One also has to consider the limitations of analog-to-digital quantization noise and other non-linearity.

This application discloses a novel non-uniform sampling technique for a burst type signal. The analog signal is digitized with high sampling rate to maintain harmonics at higher frequencies and consequently the integrity of the analog signal. Then by using non-uniform sampling technique the most significant samples are selected for further processing which results in overall cost and power consumption reduction.

BRIEF DESCRIPTION OF THE DRAWINGS

FIG. 13 depicts non-uniform sampling circuit block diagram

FIG. 14 illustrate a non-uniform sampling method

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1:
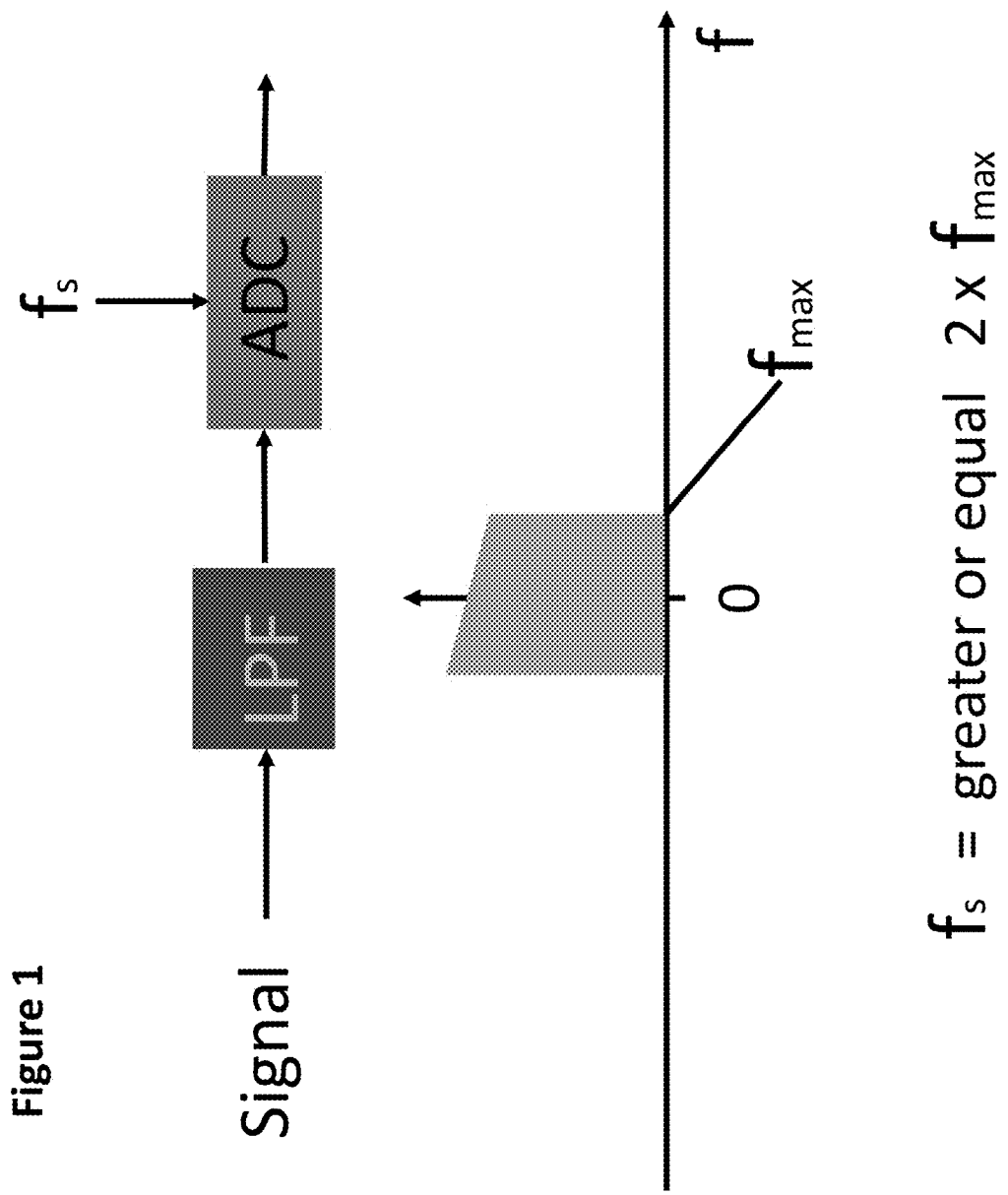
FIG. 1 illustrate Nyquist sampling
Figure 2:
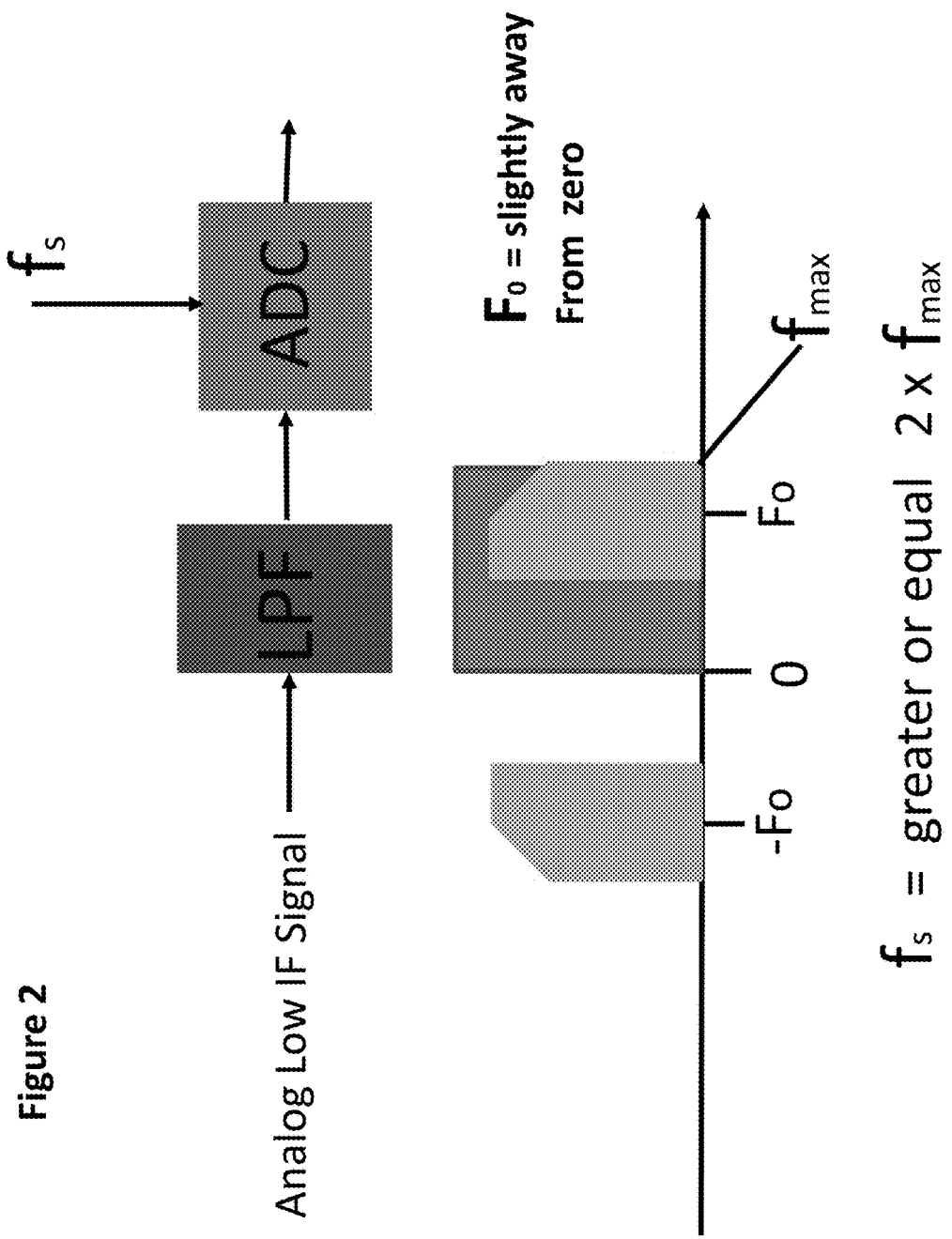
FIG. 2 shows low IF sampling
Figure 3:
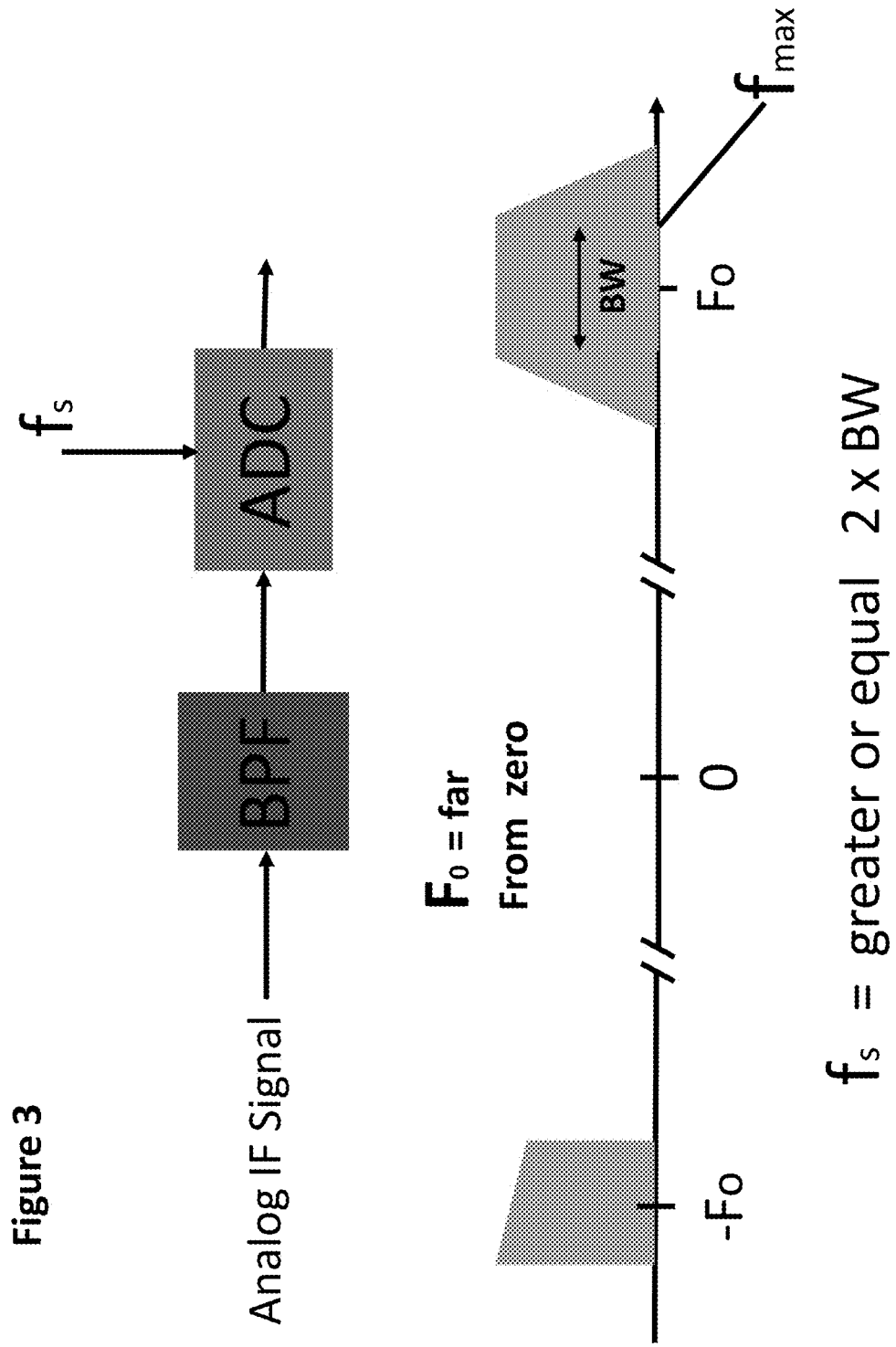
FIG. 3 shows sub-harmonic IF sampling
Figure 4:
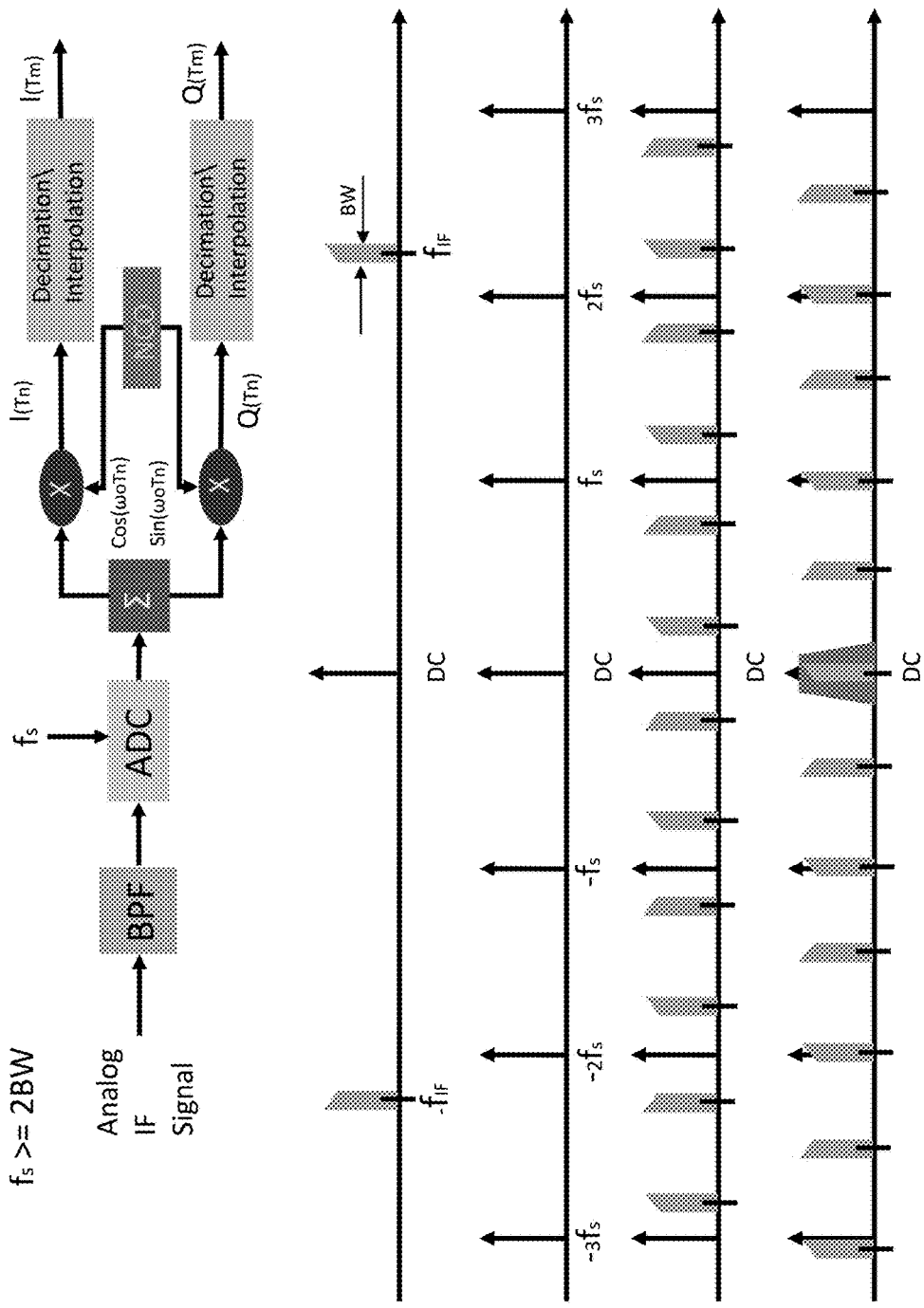
FIG. 4 illustrate detail of sampling frequency for sub-harmonic IF sampling
Figure 5:
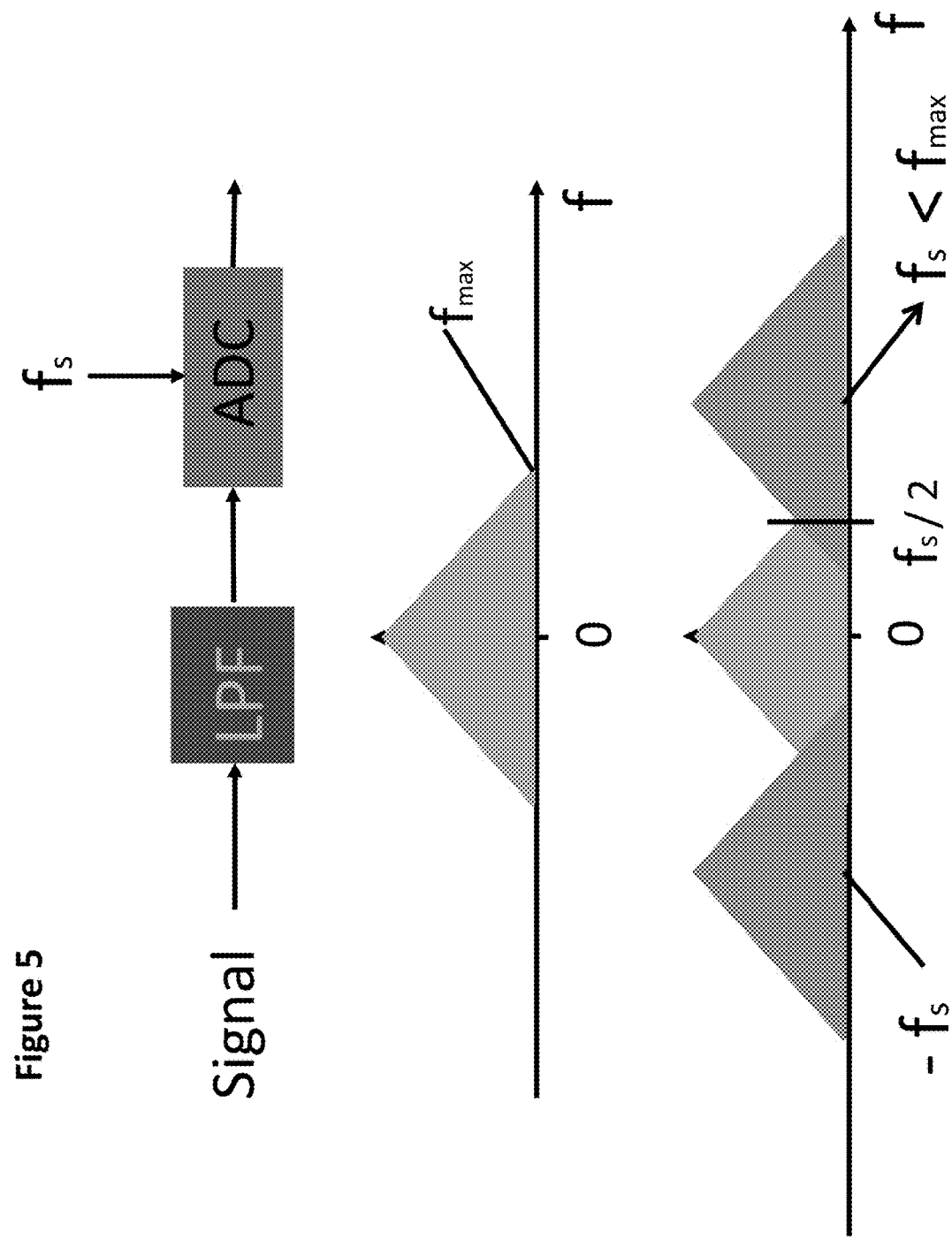
FIG. 5 shows the effect of aliasing due to under sampling
Figure 6:
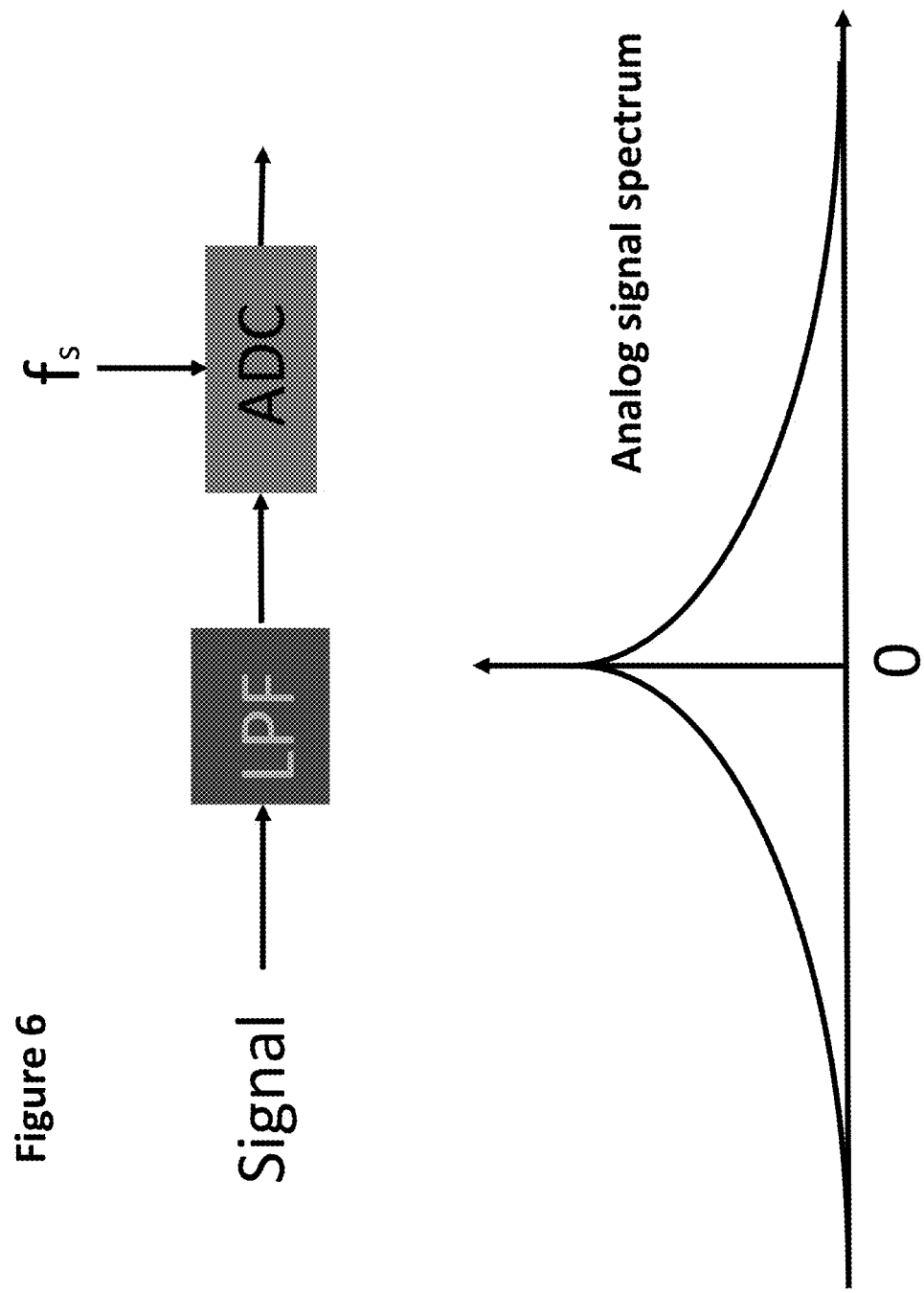
FIG. 6 shows the spectrum of a burst type analog signal
Figure 7:
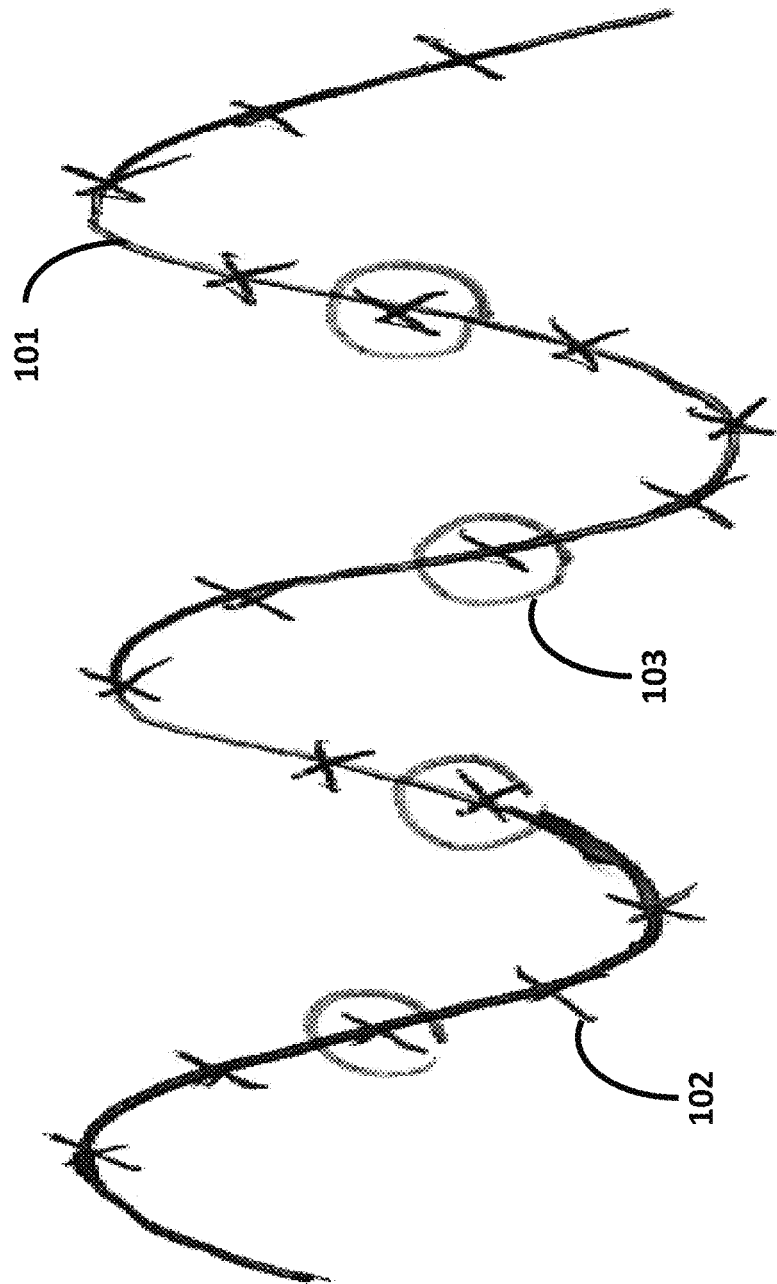
FIG. 7 illustrates a sampled sinusoidal signal

FIG. 7 depicts an over sampled signal 100. A sinusoidal signal 101 is over sampled and represented by samples 102. According to Nyquist theorem for sinusoidal signal 101 only two samples per period is requires. Therefore circled samples 103 for sinusoidal signal 101 are redundant.

In one embodiment of over sampled signal 100, the redundant samples 103 can be identified and removed without loss of signal fidelity.

Figure 8:
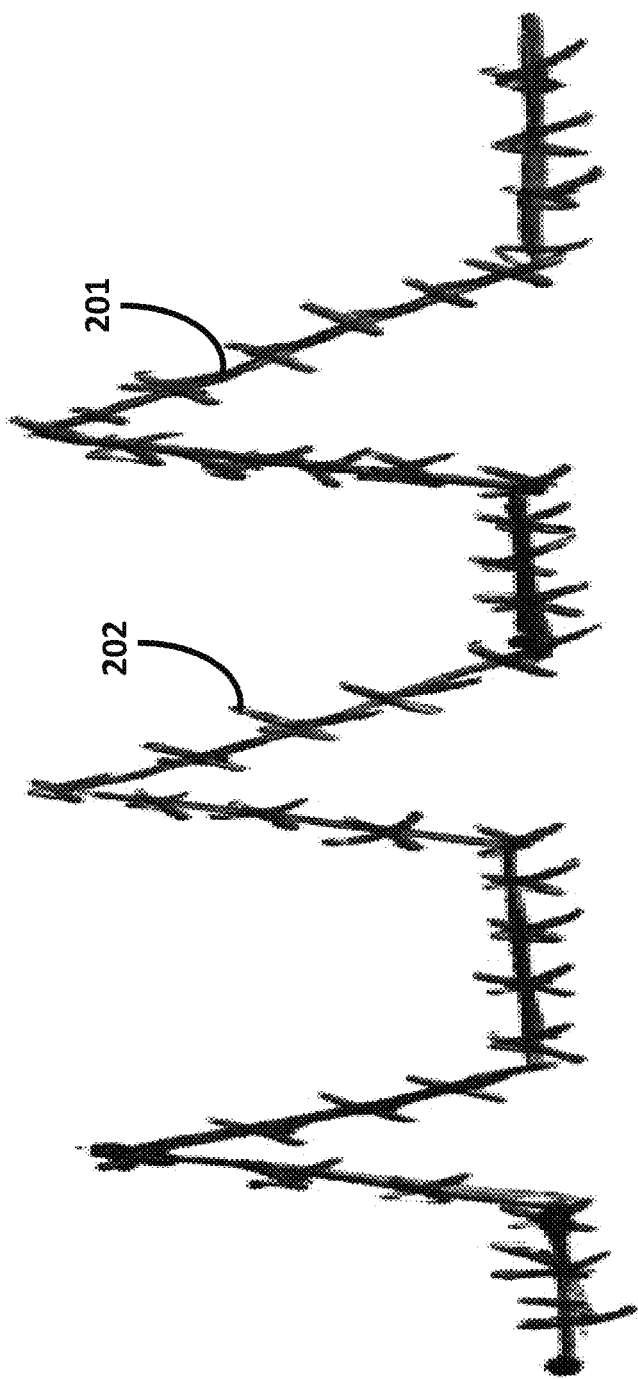
FIG. 8 depicts an over sampled bust type signal

FIG. 8 illustrate a sampled burst signal 200. The burst signal comprises of periodic bursts 201. The burst signal 200 is sampled based on Nyquist theorem and represented by samples 202. It is clear from periodic burst signal 201 that there are considerable redundant samples 202 during one period of the burst both in the flat part of the period and during the burst.

Figure 9:
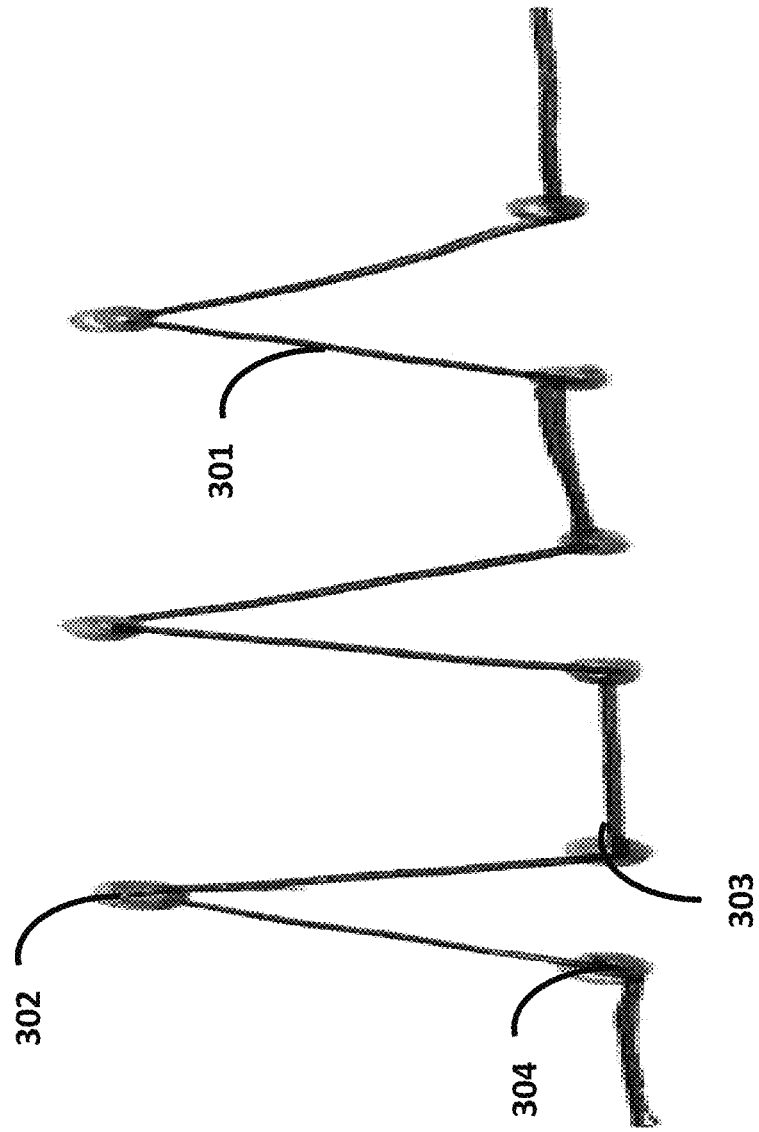
FIG. 9 shows the required samples for a burst type signal

FIG. 9 illustrate a sampled burst signal 300. The burst 301 does not require multiple samples for most of its period except during the time it burst. There are three sample points 302, 303, and 304 in burst 301 that carry the required information for continued processing.

In one embodiment of burst signal 300, sample 304 at the start of burst 301, sample 302 at the peak of the burst 301, and sample 303 at the end of the burst 301 are sufficient for further processing of a burst signal.

Figure 10:
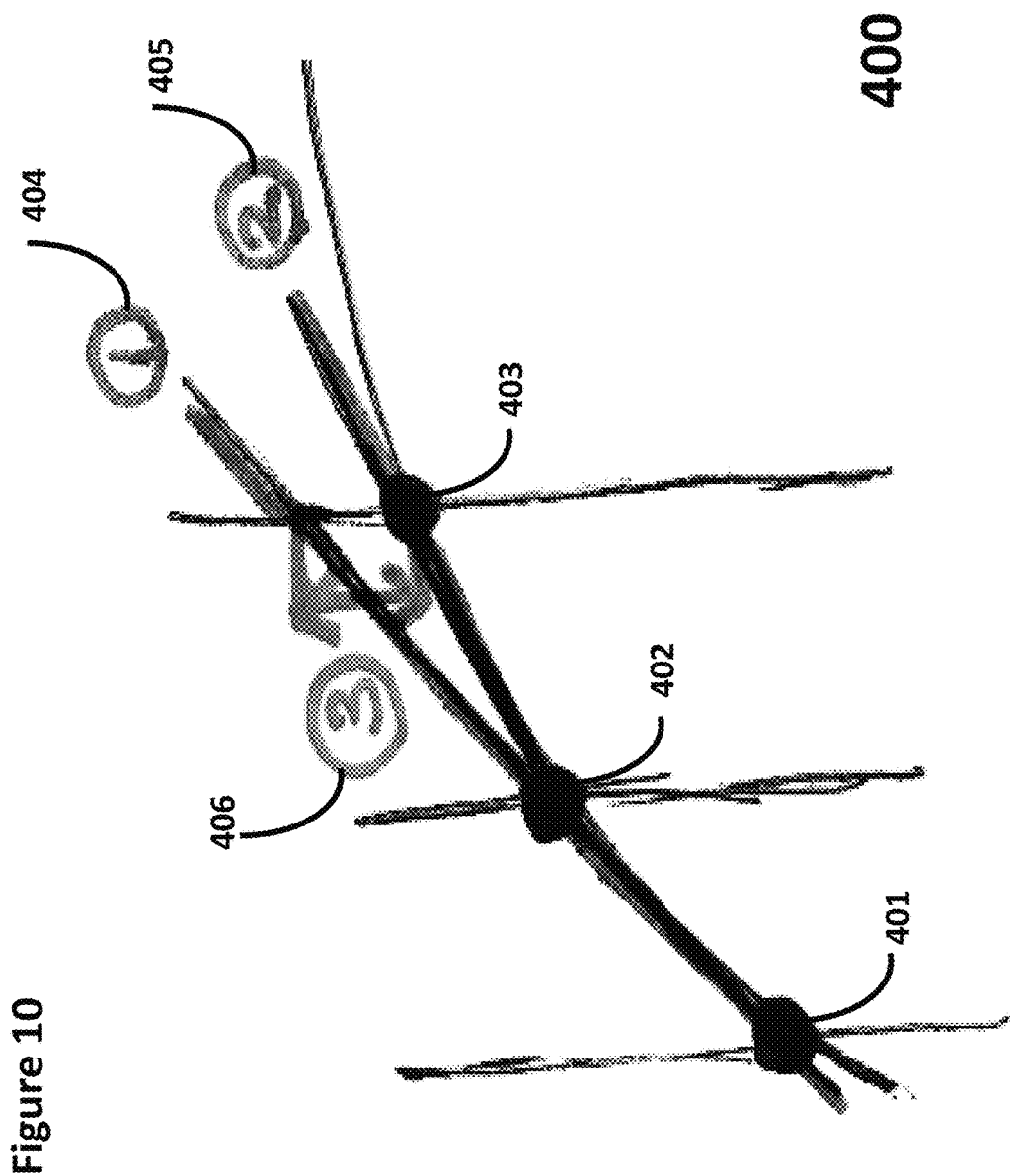
FIG. 10 illustrate derivative of consecutive samples

FIG. 10 depicts consecutive sample pairs derivative 400. Derivative of two samples 401 and 402 results in slop 404 and derivative of two samples 402 and 403 results in slop 405. If the difference between these two derivative 406 is zero or negligible then sample 402 can be eliminated.

In one embodiment of consecutive sample pair derivative 400, consecutive sample pair derivatives is used to determine which sample of an analog signal can be eliminated without loss of signal fidelity.

Figure 11:
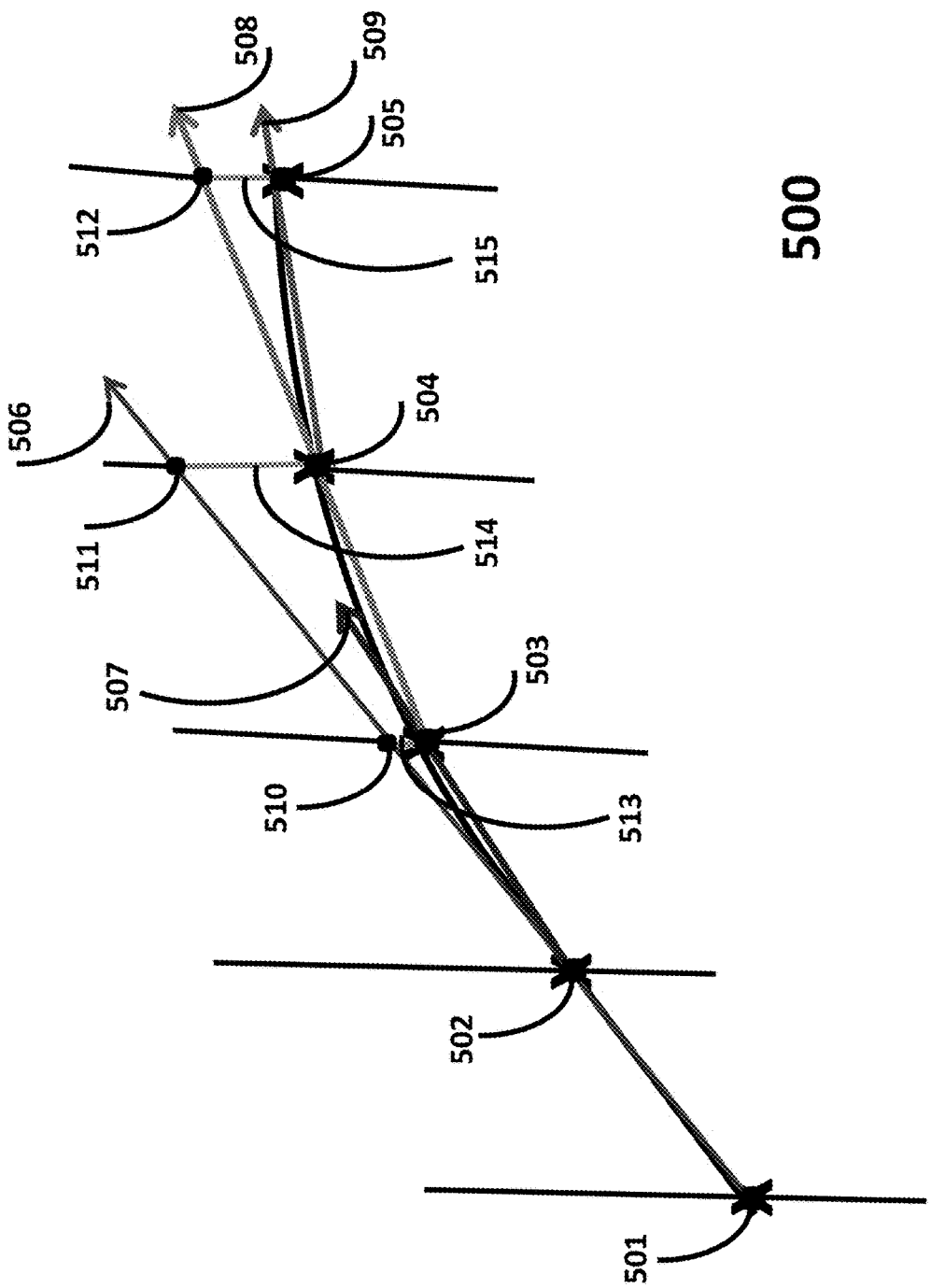
FIG. 11 depicts how to reduce the number of uniform samples

FIG. 11 illustrate a non-uniform sampling technique 500. In general non-uniform sampling 500 facilitates elimination of samples in an over sampled analog signal using derivatives of consecutive sample pairs. The samples 501, 502, 503, 504, and 505 of an over sampled analog signal are used to find slops 506, 507, 508, and 509, determine estimated values 510, 511 and 512 for samples 503, 504 and 505, and calculate differences 513, 514, and 515 between estimated values 510, 511 and 512 and the real values 503, 504, and 505 respectively. Derivative of sample pair 501 and 502 results in slop 506, derivative of sample pair 502 and 503 results in slop 507, derivative of sample pair 503 and 504 produces slop 508, and derivative of sample pair 504 and 505 results in slop 509. Slop 506 is used to find estimated value 510 for sample 503. If 513 the difference between real value of sample 503 and the estimated value 510 is smaller than a specified threshold, it allows sample 502 to be eliminated. Since sample 502 is eliminated slop 506 represents the derivative of sample pair 501 and 503 and is used to find an estimated value 511 for sample 504. The difference 514 between real value of sample 504 and its estimated value is higher than a specified threshold and therefore, sample 503 is not eliminated. Slop 508 representing derivative of sample pair 503 and 504 is used to find an estimated value 512 for sample 505. Since the difference 515 between real value of sample 505 and its estimated value 512 is higher than a specified threshold sample 505 is kept and the process continues for following samples.

In one embodiment of non-uniform sampling technique 500, a derivative of a pair of consecutive samples is used to calculate the slop of the line connecting the two samples In one embodiment of non-uniform sampling technique 500, the slop of the line connecting a pair of consecutive samples is used to find an estimated value for the sample followed the pair of consecutive samples.

In another embodiment of non-uniform sampling technique 500, the difference between the estimated value and real value of the sample followed the pair of consecutive samples is used to decide whether the second sample in the pair of consecutive samples can be eliminated.

In one embodiment of non-uniform sampling technique 500, a threshold for the difference of the estimated and the real value of the sample followed the pair of consecutive samples is used to decide if the second sample in the pair of consecutive samples can be eliminated.

Figure 12:
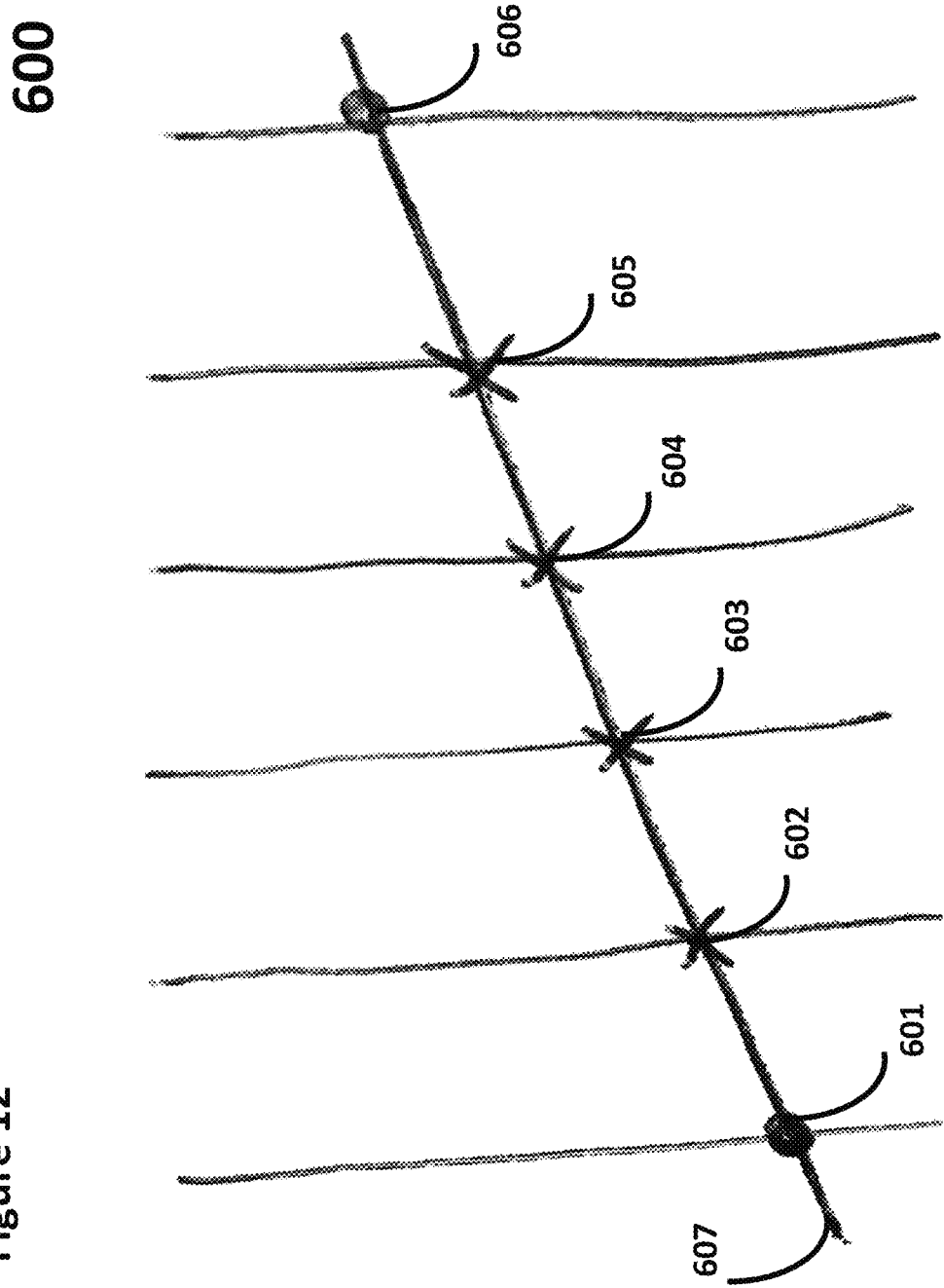
FIG. 12 shows the case when the slop of consecutive samples has minimum change

FIG. 12 shows sample elimination criteria 600. In general sample elimination criteria is based on a threshold which depends on type of analog signal and the amount of over sampling. Samples 601, 602, 603, 604, 605, and 606 represent a time window of an over sampled analog signal. The difference between derivative of consecutive sample pair 601, and 602 and the consecutive sample pair 602, and 603 is below a predefined threshold and results in elimination of sample 602. The difference between derivative of consecutive sample pair 601, and 603 and the consecutive sample pair 603, and 604 is also below a predefined threshold and results in elimination of sample 603. If this process is continued samples 602, 603, 604 and 605 are eliminated. However, the number of samples in a row that can be eliminated depends on the fidelity and integrity of over sampled analog signal and need to be limited to an acceptable number.

In one embodiment of sample elimination criteria 600, the number of samples in a row that can be eliminated needs to be limited to a figure that the fidelity and integrity of over sampled analog signal is maintained.

FIG. 13 depicts block diagram a non-uniform sampling system 700. In general non-uniform sampling system 700 facilitates operation with lower cost and power consumption. By lowering the number samples from an over sample analog signal 701, at the output of analog-to digital converter 702, using a non-uniform sampling algorithm 703, only samples with maximum information are selected for processing, transmission to other entities 704 and 705 is simplified, and further processing by an intermediate device 704 and doctor dashboard 705 is minimized.

In one embodiment of non-uniform sampling 700, includes, among other things, ADC 702, non-uniform sampling algorithm processor 703, intermediate device 704 and doctor dashboard 705.

In one embodiment of non-uniform sampling 700, the analog signal 701 has a spread frequency domain spectrum 706 that can't be limited by anti-aliasing filter.

In one embodiment of non-uniform sampling 700, the over sampling frequency used by analog-to-digital convertor (ADC) 702 is high enough to transfer maximum information to digital domain.

In one embodiment of non-uniform sampling 700, the samples at the output of ADC is used by non-uniform sampling processor 703 to select samples with needed information for further processing.

In another embodiment of non-uniform sampling 700, the non-uniform sampling algorithm 703 uses the difference of consecutive sample pair's derivatives to determine if a sample can be eliminated.

In one embodiment of non-uniform sampling 700, the intermediate device 704 monitors the data it receives from non-uniform sampling processor 703 and processes them for displaying graphically.

In one embodiment of non-uniform sampling 700, the communication between non-uniform sampling processor 703 and intermediate device 704 is wireless or wire line.

In another embodiment of non-uniform sampling 700, the intermediate device 704 communicates its data to a doctor dashboard through the Internet network or wirelessly.

In one embodiment of non-uniform sampling 700, the non-uniform sampling system 700 can be used to monitor heart electrocardiogram (ECG).

In another embodiment of non-uniform sampling 700, the non-uniform sampling system 700 can be used by biometric devices, like blood pressure measurement, and heart beat measurement.

In one embodiment of non-uniform sampling 700, the non-uniform sampling system 700 can be used by various sensors used for robotic, automobile, and flying objects.

In another embodiment of non-uniform sampling 700, the non-uniform sampling system 700 can be used in conjunction with Artificial Intelligence (AI).

In another embodiment of non-uniform sampling 700, the non-uniform sampling 700 is used by ambient sensor nodes, like temperature, humidity, light.

In another embodiment of non-uniform sampling 700, the non-uniform sampling 700 is used by low power sensor networks, to pre-estimate sensor values to minimizing connection to sensor nodes.

FIG. 14 depicts an embodiment of method 800 for using the derivative of consecutive sample pairs in non-uniform sampling. In various embodiments, method 800 is carried out by processor, analog-to-digital convertor, and analog circuit under the control of processes or executable instructions. The readable and executable instructions reside, for example, in a data storage medium such as processor usable volatile and non-volatile memory. However, the readable and executable instructions may reside in any type of processor readable storage medium. In some embodiments, method 800 is performed at least by one of the circuits described herein.

At 801 of method 800, over sample the analog signal and start non-uniform sampling algorithm.

At 802 of method 800, subtract derivative of first and second samples from derivative of second and third samples to find an estimated value for third sample.

At 803 of method 800, If the difference between estimated and real value of sample 3 is below a threshold then eliminate sample 2 and continue the 802 process for sample 1, 3 and 4.

At 804 of method 800, If the difference between estimated and real value of sample 3 is not below a threshold then continue the 802 process for sample 2, 3 and 4.

At 805 of method 800, once the non-uniform sampling process is completed, continue with processing signal with lower samples and send the results to artificial intelligence.

Various embodiments are thus described. While particular embodiments have been described, it should be appreciated that the embodiments should not be construed as limited by such description, but rather construed according to the following claims.

The invention claimed is:

1. A digital circuit to perform non-uniform sampling by eliminating a redundant sample comprising:
an analog-to-digital convertor to convert an analog signal to a digital signal represented by a digital sample, a computing machine with a memory that receives the digital samples and executes an algorithm to eliminate a redundant digital sample, and a threshold value configured in said memory that is used as a reference for identifying said redundant digital sample;
said algorithm comprising:
a program to calculate a derivative of two of said digital samples by dividing a difference of values of said digital samples with a difference of time said digital samples are taken;
wherein said program then calculates a difference of two said consecutive derivatives using three of said consecutive digital samples that are not eliminated with the second digital sample as a common digital sample in two said consecutive derivatives;
wherein the program further compares said difference of two said consecutive derivatives with said threshold value and if the difference of two said consecutive derivatives is larger or equal to said threshold value the common digital sample used in two said consecutive derivatives is redundant and will be eliminated; and
the digital samples that are not eliminated are used for further processing.

2. The digital circuit explained in claim 1, wherein two of said digital samples are a number of sample clocks apart due to said redundant digital sample or samples between them that are eliminated.

3. The digital circuit explained in claim 1, wherein said analog signal is burst type.

4. The digital circuit explained in claim 1, wherein said analog signal is burst type and periodic.

5. The digital circuit explained in claim 1, wherein a number of said consecutive redundant digital samples depends on the threshold value.

6. The digital circuit explained in claim 1, wherein said digital circuit to perform non-uniform sampling is used in Electrocardiogram (ECG) biometric devices.

7. The digital circuit explained in claim 1, wherein said digital circuit to perform non-uniform sampling is used by biometric devices, like blood pressure measurement, and heart beat measurement.

8. The digital circuit explained in claim 1, wherein said digital circuit to perform non-uniform sampling is used by various sensors used for at least one of robot, automobile, and flying objects.

* * * * *